US00PP10919P

United States Patent [19]

Zaiger et al.

[11] Patent Number: Plant 10,919

[45] Date of Patent: May 25, 1999

[54] NECTARINE TREE NAMED 'ARCTIC MIST'

[76] Inventors: Chris Floyd Zaiger, 929 Grimes Ave.; Leith Marie Gardner, 1207 Grimes Ave.; Gary Neil Zaiger, 1907 Elm Ave.; Grant Gene Zaiger, 4005 California Ave., all of Modesto, Calif. 95358

[21] Appl. No.: 08/961,936

[22] Filed: Oct. 31, 1997

[51] Int. Cl.[6] ..... A02H 5/00

[52] U.S. Cl. ..... Plt./189

[58] Field of Search ..... Plt./40.1, 189

*Primary Examiner*—Howard J. Locker
*Assistant Examiner*—Ashwin Mehta

[57] ABSTRACT

A new and distinct variety of nectarine tree (*Prunus persica* var. *nucipersica*) which has the following unique combination of features that are desirable in a new variety. The following features of the tree and its fruit are characterized with the tree budded on nemaguard rootstock, grown on Hanford sandy loam soil with Storie Index rating 95, in USDA hardiness zone 9, near Modesto, Calif., and with standard commercial cultural fruit growing practices, such as, pruning, thinning, spraying, irrigation, fertilization, etc.:

1. Vigorous, upright growth.
2. Heavy and regular production of fruit.
3. Fruit ripening in the late maturity season.
4. Produces large, freestone, white flesh fruit.
5. Fruit having excellent flavor and eating quality.
6. Fruit having firm flesh with good handling and shipping qualities.
7. Extending the California white flesh nectarines maturity season by approximately 9 days with commercial quality fruit.

1 Drawing Sheet

ORIGIN OF THE VARIETY

The present new and distinct nectarine variety was originated by us in our experimental orchard located near Modesto, Calif., as a selected seedling from an open pollinated 'Arctic Snow' Nectarine (U.S. Plant Pat. No. 7,920) seed. A large group of these open pollinated seedlings were grown by us and maintained under close observation, one such late maturing seedling, which is of the present variety, having especially desirable fruit characteristics, tree growth habit and productivity when growing on its own root, was selected for asexual reproduction and commercialization.

ASEXUAL REPRODUCTION OF THE VARIETY

Asexual reproduction of the new and distinct variety of nectarine tree was by budding to nemaguard rootstock, the standard rootstock for peaches and nectarines in California, as performed by us in our experimental orchard located near Modesto, Calif., and shows that all characteristics of the tree and its fruit run true to the original tree and are established and transmitted through succeeding asexual propagations.

SUMMARY OF THE VARIETY

The new and distinct variety of nectarine tree is of large size, vigorous, upright growth and a regular and productive bearer of large, firm, white flesh, freestone fruit with excellent flavor and eating quality. The fruit is further characterized by having good handling and shipping qualities, the ability to remain firm on the tree 7 to 8 days after maturity (shipping ripe) and, in comparison to the late maturing white flesh 'Arctic Snow' Nectarine (U.S. Plant Pat. No. 7,920), the new variety is approximately 9 days later in maturity.

PHOTOGRAPH OF THE VARIETY

The accompanying color photographic illustration shows typical specimens of the foliage and fruit of the present new nectarine variety. The illustration shows the upper and lower surface of the leaves, an exterior and sectional view of a fruit divided in its suture plane to show flesh color, pit cavity and the stone remaining in place. The photographic illustration was taken shortly after being picked (shipping ripe) and the colors are as nearly true as is reasonably possible in a color representation of this type.

DESCRIPTION OF THE VARIETY

The following is a detailed botanical description of the new variety of nectarine tree, its flowers, foliage and fruit, as based on observations of specimens grown near Modesto, Calif., with color terminology (except those in common terms) in accordance with Reinhold Color Atlas by A. Kornerup and J. H. Wanscher.

Tree:

*Size.*—Large— Height and width pruned to 12 to 14 feet for economical harvesting.

*Vigor.*—Vigorous — developing 5½' to 7' of growth in first growing season. During first dormant season the tree is pruned to 4 to 5 feet in height when selecting primary branches for desirable scaffolds and to promote proper tree growth for secondary scaffolds to be selected during pruning in second dormant season.

*Form.*—Usually pruned to vase shape.

*Productivity.*—Productive — fruit set is twice or more of what is desirable for normal tree crop load and fruit is thinned and properly spaced to develop desirable market size. Number of fruit set usually varies with amount of winter chilling and spring water condition during bloom time.

*Bearer.*—Regular.

*Density.*—Medium dense. The tree is medium dense, pruned to the standard fruit tree vase shape to allow air and sunlight to penetrate the center of the tree to help the fruit off-set fungus and diseases such as brown rot, give more color and Brix to the fruit, etc..

*Growth.*—Upright. The normal upright growth habit of the tree would be approximately twice the height if it was allowed unrestricted growth. Under most fruit cultural practices fruit trees are pruned to 12 to 14 feet in height and 12 to 14 feet in width for economical harvesting.

*Hardiness.*—Winter chilling requirement is approximately 850 hours below 45° F. Hardiness tested in USDA Hardiness Zone 9.

Trunk:

*Size.*—Medium stocky.

*Texture.*—Medium shaggy.

*Color.*—Grayish brown to brown (6-E-4) to (6-E-6). Varies with age of tree.

Branches:

*Size.*—Medium stocky.

*Texture.*—Smooth to medium rough. Varies with age of growth.

*Lenticels.*—Numerous. Medium size.

*Color.*—Light brown to brown (6-D-4) to (6-D-5).

Leaves:

*Size.*—Large. Average length 5¾". Average width 1¾".

*Form.*—Lanceolate. Pointed.

*Margin.*—Crenate.

*Thickness.*—Medium.

*Surface.*—Smooth.

*Petiole.*—Medium length. Medium thickness.

*Glands.*—Reniform. Number varies from 2 to 5. Average number 3. Medium size. Located on base of leaf blade and upper portion of petiole.

*Color.*—Upper surface — green to deep green (27-D-8) to (27-E-8). Lower surface — grayish green to dull green (29-D-5) to (29-D-8).

Flower buds:

*Size.*—Medium to large.

*Length.*—Medium.

*Form.*—Plump.

Flowers:

*Size.*—Large, showy. 1½" to 1⅝" diameter.

*Pollen.*—Present. Self-fertile.

*Blooming period.*—Date of first bloom Feb. 29, 1996. Date of last bloom Mar. 5, 1996. Varies slightly with climatic conditions.

*Color.*—Pink to light pink (11-A-2) to (11-A-3). Varies with age of bloom.

Fruit:

*Maturity when described.*—Firm ripe.

*Date of first picking.*—Sep. 10, 1996.

*Date of last picking.*—Sep. 18, 1996.

*Size.*—Large. Average diameter axially 2⅞" to 3⅛". Average transversely in suture plane 2⅞" to 3". Average weight 220 grams, varies from 220 to 235 grams.

*Form.*—Nearly globose, only slightly elongated.

*Suture.*—Shallow, extends from base to apex.

*Ventral surface.*—Nearly round, only very slightly lipped.

*Apex.*—Varies from round to very slight pistil point.

*Base.*—Retuse.

*Cavity.*—Slightly elongated in suture plane. Average depth ½". Average breadth 1".

Flesh:

*Ripens.*—Evenly.

*Texture.*—Firm.

*Fibers.*—Few, tender.

*Aroma.*—Slight.

*Amygdalin.*—Undetected.

*Eating quality.*—Excellent.

*Flavor.*—Excellent, sweet, subacid, mild.

*Soluble solids.*—Brix range 14.1 to 17.1. Average Brix 16.4.

*Juice.*—Moderate amount, good balance, sweet, enhancing eating quality.

*Color.*—White (10-A-1). Pit cavity — brownish-red to strawberry red (10-D-6) to (10-D-8), with bleeding of red from pit cavity into flesh, heavier toward the suture.

*Down.*—Wanting.

*Tendency to crack.*—None.

*Color.*—Yellowish-white to pale yellow (4-A-2) to (4-A-3). Partially overspread with deep red to strawberry red (10-C-8) to (10-D-8).

Stone:

*Type.*—Freestone.

*Size.*—Large. Average length 1⅛". Average width 1". Average thickness ¾".

*Form.*—Obovoid.

*Base.*—Usually straight, varies from straight to slightly rounded.

*Apex.*—Pointed.

*Surface.*—Irregularly furrowed toward apex, pitted toward base. Pits vary from round to elongated. Most stones have a long groove along the suture, with varying depths.

*Sides.*—Varies from equal to unequal. Some stones are unequal with one side being slightly larger in size and having deeper furrows and pit cavities.

*Tendency to split.*—None.

*Color.*—Mahogany to reddish brown (8-E-7) to (8-F-8).

Use: Dessert. Market, local and long distance.

Keeping quality: Good. Held well in storage for 3 weeks after picked and packed.

Shipping quality: Good. The firm flesh revealed minimal bruising or scaring of flesh or skin in packing and shipping trials.

The present new variety of nectarine tree, its flowers, foliage and fruit herein described may vary in slight detail due to climate, soil conditions and cultural practices under which the variety may be grown. The present description is that of the variety grown under the ecological conditions prevailing near Modesto, Calif.

We claim:

1. A new and distinct variety of nectarine tree, substantially as illustrated and described, characterized by its large size, vigorous, upright growth, and a productive and regular bearer of large, white flesh, freestone fruit that has the ability to remain firm on the tree 7 to 8 days after maturity; the fruit is further characterized by its good handling and shipping quality, its sweet, subacid flavor and, in comparison to the late maturing, white flesh variety 'Arctic Snow' Nectarine (U.S. Plant Pat. No. 7,920), the fruit of the new variety is approximately 9 days later in maturity.

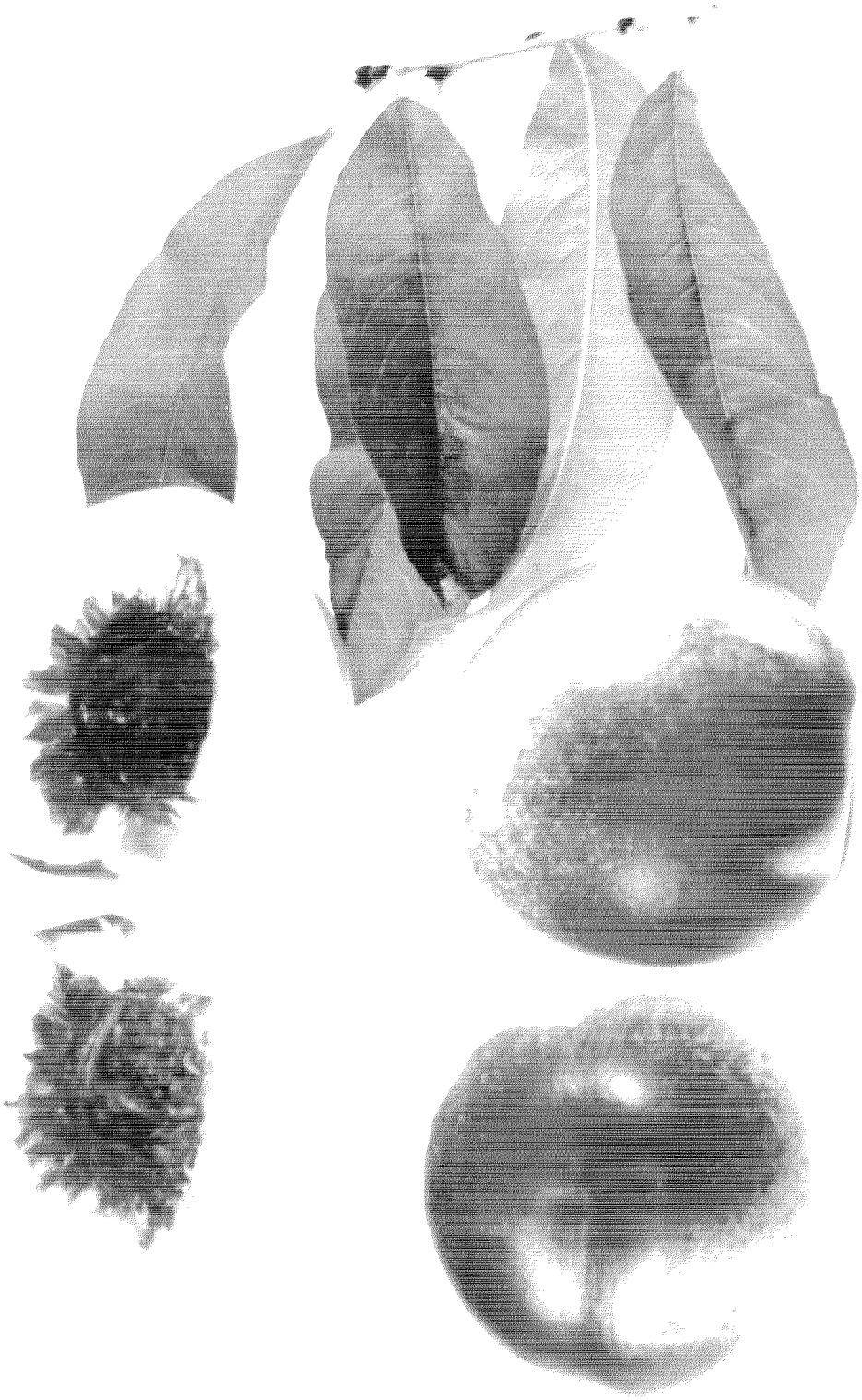

* * * * *